United States Patent [19]

De Beer

[11] Patent Number: 5,275,051
[45] Date of Patent: Jan. 4, 1994

[54] METHOD AND SYSTEM FOR NONDESTRUCTIVE TESTING OF RAILROAD CROSSTIES

[75] Inventor: Harry T. De Beer, Oakville, Canada

[73] Assignee: Tiescan, Inc., Cherry Hill, N.J.

[21] Appl. No.: 758,868

[22] Filed: Sep. 11, 1991

[51] Int. Cl.$^5$ .................. G01N 29/08; G01N 29/18; G01N 29/20
[52] U.S. Cl. ........................ 73/598; 73/600; 73/634; 73/639
[58] Field of Search ............ 73/597, 598, 599, 600, 73/618, 619, 633, 634, 635, 636, 639, 628

[56] References Cited

U.S. PATENT DOCUMENTS

| | | | |
|---|---|---|---|
| 4,593,569 | 6/1986 | Joy | 73/636 |
| 4,932,618 | 6/1990 | Davenport et al. | 73/636 |

OTHER PUBLICATIONS

"PANLOGGER ® A Revolutionary New Device to Test Timber Sleepers in Track", Brochure by Pandrol Limited, 1989, pp. 1-2.
"James V-Meter Material Testing", Brochure by James Instruments Inc. Nondestructive Testing Systems, pp. 1-4.
"USL 33 Low Frequency Ultrasonic Instrument with High Penetration Power", Brochure by Krautkrämer—A Krautkrämer Branson Company, Apr. 1986, pp. 1-6.

Primary Examiner—Hezron E. Williams
Assistant Examiner—Rose M. Finley
Attorney, Agent, or Firm—Norbert P. Holler

[57] ABSTRACT

A method and system for nondestructively testing in a continuous sequence a multiplicity of railroad track crossties of wood or concrete to determine the condition and life expectancy of each of the crossties and of the track as a whole. The system includes an electric pulse generator and a pair of transmitting and receiving transducers, which transducers are adapted to be brought into moving contact with the crossties at respective locations straddling desired test regions thereof, for example, the regions under a tie plate, for sending sonic mechanical pulses through that region of the crosstie from one transducer to the other. If desired, three pairs of transducers may be provided for simultaneously straddling both tie plates and a medial reference zone on each crosstie. The transducers and the pulse generator are carried by a vehicle riding on the track rails, along with a computer for processing-/evaluating/storing/reproducing the test data. Devices for sensing the presence of each crosstie, for sweeping the same clear of ballast and debris at each of the transducer contact locations, and for marking each crosstie determined to be defective are also provided on the vehicle.

17 Claims, 6 Drawing Sheets

METHOD AND SYSTEM FOR NONDESTRUCTIVE TESTING OF RAILROAD CROSSTIES

This invention relates to a method and system for nondestructive testing of railroad crossties, and in particular to such a method and system which can be used to determine the condition and life expectancy of wood and concrete railroad crossties.

BACKGROUND OF THE INVENTION

The rails of railroad tracks are conventionally laid down on transverse beams or crossties, which traditionally have been made of wood but lately are frequently also made of concrete, and which support the rails and with the aid of tie plates and other accessories prevent the rails from spreading apart. Although exact numbers are difficult to come by, a reasonable estimate would be that there are roughly one billion crossties currently in service on the North American continent (U.S. and Canada).

The physical condition of railroad crossties, which are subjected to high levels of dynamic loading by passing trains and are exposed to almost constantly changing ambient weather conditions and temperatures, tends to deteriorate with time. The deterioration may be either a degree of decay or the occurrence of some mechanical damage, and such deterioration may take place on the surface or in the interior of the ties. Thus, the condition of railroad crossties requires close monitoring, because their deterioration and resultant failure can lead to train derailments with possibly serious and even disastrous consequences to human lives, railroad equipment, public and private property, and the environment.

Heretofore, the traditional method of determining the condition of railroad crossties and whether or not they require replacement has involved periodic visual inspections of the ties carried out by the railroad companies' tie inspectors. These inspectors "walk the track" and visually examine each and every crosstie, looking for obvious signs of decay/deterioration and physical damage of the top surface of the crossties (for all practical purposes, the top of a tie other than the regions thereof beneath the rail-locating tie plates is the only accessible surface because the bottom rests on the track bed and the sides are usually covered by ballast). Ties deemed no longer suitable for continued service are marked and subsequently replaced.

However, because the covered top and side regions and the interiors of the ties are hidden from view, it is evident that the tie inspectors perform their inspections under less than the most favorable conditions, and that their decisions to designate crossties as unfit for service are frequently based on guesswork and erroneous evaluations. In fact, it is acknowledged in the railroad industry that up to about 20% of all crossties which are replaced are replaced unnecessarily, as proven by subsequent destructive examination (cross-sectioning) after removal. The principal reason why such an unwarranted economic loss is incurred is, of course, that the outside appearance of a crosstie is not always indicative of the tie's actual condition: for example, a tie may be superficially sound but decayed or cracked internally or at the bottom, and yet neither of these conditions would be visually detectable from above; on the other hand, a tie may show some superficial deterioration or damage, e.g., a split, at the top surface and yet be perfectly sound internally or at worst only minimally deteriorated and suitable for a number of additional years of service. Moreover, the economic cost of visual inspection is further heightened by virtue of the fact that, given the need for looking closely at each tie individually and for probing the same in case of doubt, a tie inspector even at best can inspect an average of about six miles of track per day.

Another known method of inspecting wood railroad crossties, which has been developed relatively recently, utilizes an instrument which is available under the designation "PANLOGGER" from Pandrol Limited of London, England. This instrument consists of a unit that receives, processes and stores information, and a probe which makes contact with the top surface of the tie to deliver thereto controlled impacts that vibrate the tie. In theory, the response is a measure of the vibration characteristics of the tie and, because those characteristics are affected by the presence or absence of decay or mechanical damage, of the need for replacing the tie. In practice, however, this method makes use of an analysis which is based on empirical data pertaining to the particular wood species (e.g., oak, maple, sweetgum, pine, etc.) of which the tie is made. Accuracy of the method thus is open to question, because empirical data valid for all possible cases are scarce and because, given the fact that there is a considerable variation in properties within each wood species, such empirical data are also unreliable.

Moreover, this method also results only in an evaluation of the average condition of the crosstie over its entire length and does not provide a determination of which part and how much of the tie is defective. The average condition of a crosstie, however, as will be readily apparent to those skilled in the art, is not a reliable measure of its suitability for continued service. Thus, a crosstie with very minor internal decay throughout its length, or a crosstie with minor degrees of decay under both tie plates but otherwise sound, or a crosstie with severe decay under one tie plate but otherwise sound throughout its length, all may provide the same average vibration response and thereby indicate the same average condition, yet the first one may be suitable for many more years of service, the second one may be suitable for at least several more years of service, and the third one may be totally unacceptable for any further service. Over and above this stands the fact that this method has been developed for use in conjunction with visual inspection, so that the previously mentioned time requirements for such an inspection are not ameliorated.

Another known device which has been suggested to be usable for testing concrete and wood structures, including wood railroad ties, is a low frequency ultrasonic tester available under the designation "JAMES V-METER" from James Instruments Inc. of Chicago, Ill. This device has been promoted as being capable of performing sonic pulse velocity measurements on coarse grain materials such as concrete and wood, among others, using pairs of various types of transducers (including both standard and rolling transducers), as being portable and of light weight, as being adapted for both A.C. and D.C. operation, and as providing direct digital readout of pulse transit time as well as digital printouts. However, the device is only adapted for manually performed individual spot testing procedures, which would be even slower than those performed with "PANLOGGER" instrument and so inefficient in a crosstie-testing environment as to be unacceptable, and which, apart from a time reading, provides no direct indication of the quality of the test object. Thus, the device cannot evaluate a length of railroad track including many crossties for overall integrity, nor can it provide an indication of the life expectancy of the individual crossties at a high rate.

Yet another known device which has been promoted as being suitable for testing objects of coarse grain structures by utilizing ultrasonic pulses applied through spaced probes or transducers to test objects of, among other materials, wood and concrete, is available under the designation "USL 33" from Krautkramer Branson of Lewistown, Pa. However, this device is also not designed to evaluate a length of railroad track including many crossties continuously at a high rate.

BRIEF DESCRIPTION OF THE INVENTION

It is the principal object of the present invention to provide a system and method for nondestructively testing wood and concrete railroad crossties for decay and mechanical damage both interiorly and exteriorly and for thereby determining their condition and life expectancy, which are more efficient and economical to implement than, and avoid the mentioned drawbacks and disadvantages of, the known crosstie inspection and testing systems and methods.

It is another object of the present invention to provide such a system and method by which the regions of a crosstie that are most vulnerable to decay and mechanical damage, i.e., the regions beneath the rails and tie plates, can be individually tested at relatively high speeds and by which, if desired, the central region of the crosstie, where the tie is least vulnerable to decay and mechanical damage, can be used as a reference datum.

It is yet another object of the present invention to provide such a system and method for crosstie inspection and evaluation the accuracy of which is not affected by environmental or other extraneous factors.

Generally speaking, the basic objectives of the present invention are achieved by a system and method as aforesaid which are characterized by the provision of a vehicle movable continuously and at a relatively high speed along a section of railroad track containing many crossties, which vehicle includes means for generating electrical pulses, transforming such pulses into sonic mechanical pulses and transmitting the latter to at least one region of each of the series of crossties being tested where internal damage and deterioration of the crossties are likely to occur, sensing the mechanical pulses in each crosstie after they have passed through the test region of that crosstie, transforming the sensed mechanical pulses into electrical pulses and analyzing the latter to obtain velocity and attenuation measurements of the sonic mechanical pulses, and determining, on the basis of the analyzed pulses, the condition and life expectancy of each of the crossties and of the track as a whole.

Within this context it is contemplated that the initially generated electrical pulses are received by a first transducer means adapted to be brought sequentially into moving contact with the crossties being tested at a first location adjacent the test region of each tie and are converted by the first transducer means into sonic mechanical pulses, at frequencies ranging from about 25 kHz to about 55 kHz but possibly to as much as about 100 kHz, which are transmitted to and travel through the test region, that the pulses travelling through each test region of each crosstie are sensed by a second transducer means disposed in moving contact with that crosstie at a second location adjacent the test region but spaced from the first location and are converted by the second transducer means into electrical pulses which are transmitted to the analyzing means, that the analyzing means measures the velocity and attenuation of the mechanical pulses travelling through each test region of each crosstie, and that these measurements are transmitted to a pre-programmed computer which compares them with reference values therefor It will be understood, in this regard, that the acoustic velocity is obtained by dividing the known distance between the two associated transducer means by the time of travel of the sonic pulses from the first to the second transducer means, the velocity determination being made by the electronic circuitry.

Within this context also, it is further contemplated that, in accordance with one embodiment of the present invention, the various components of the system may be carried by a relatively lightweight wheeled vehicle adapted to ride on the rails of the track supported by the crossties being inspected, with the vehicle either being self-propelling, i.e., equipped with a motor or engine driving its wheels, or being adapted to be propelled by hand, i.e., by being pushed or pulled along the track by a tie inspector. In this arrangement, there are then preferably provided on the vehicle suitable means for sweeping any accumulated ballast and debris off the top surface of each tie at two spaced locations straddling the respective test region to ensure a subsequent unimpeded firm contact between the tie and the two transducer means, means for supplying a sonic couplant (a low-viscosity pumpable liquid such as water, oil, or the like which should, however, be environmentally friendly) to the transducer means for forming thin films (about 3 mils thick) of the liquid at the respective interfaces of the tie and the two transducer means to ensure adequate propagation of the sonic pulses across those interfaces, and means for marking each tie determined by the computer to require future attention or to be unfit for further service. The arrangement may optionally also include means for sequentially sensing the approach of the vehicle to the test regions of the successive crossties, means for lowering the ballast sweeping means and the transducer means from a normal elevated position down to tie-top level each time a tie is sensed and for raising the sweeping and transducer means off tie-top level and back to the elevated rest position when the sensing means are passing over the intervals between successive crossties.

In a particularly sophisticated version of the system according to the present invention, the system includes a pulse generator and three sets of laterally spaced, paired transmitting and receiving transducers, which are carried by the vehicle and are adapted to be sequentially brought into moving contact with the successive crossties at respective pairs of locations straddling three desired regions thereof, for transmitting sonic mechanical pulses through those regions. The three pairs of transducers are arranged, either by virtue of being permanently disposed at tie-top level or by virtue of being mounted for joint protraction (lowering) toward or retraction (elevating) from tie-top level, to be simultaneously brought into contact with each crosstie at the three regions thereof, two pairs so as to straddle the two tie plates where, as previously mentioned, the tie is most vulnerable to deterioration and damage, and the third pair so as to straddle a central region of the crosstie where the tie is least vulnerable to deterioration and damage and which can therefore serve as a reference region. The system also includes suitable means for performing the various required functions, i.e., activating the sonic couplant feed and the transducers, processing/evaluating/storing/reproducing the test data, and activating, if appropriate, the device for marking each crosstie determined to be defective.

In the analytical aspects of the operation of the system, the computer receives and sorts the velocity and attenuation measurements of the sonic mechanical pulses traveling through the test regions of the crossties, but the computer is also programmed to discard unusually high readings (which in wood ties can be caused by knots or exceptionally hard portions of the original tree and in concrete ties can be caused by portions of excessively high compressive strength) and unusually low readings (which almost always signify inadequate coupling between the transducers and the crossties). The computer then compares the average of the readings taken at each test region (the tie plate) of each tie with the reference readings taken at the center region of the same tie. If, at either tie plate of any given tie, the reading is lower, by more than a predetermined percentage, than the associated reference reading, the computer determines how bad the condition of the tie is and signals the marking device to spray or otherwise apply onto the tie a controlled quantity of paint, the magnitude of the area or length of the applied spray serving to indicate what the life expectancy (and hence the urgency of the need for replacement) of the tie is. In the course of a complete run, the computer also makes a determination of the overall integrity of the track, providing, storing and printing out, among other information, data representing pulse velocity measurements and attenuation losses and paint spray system actions, data describing the proximity of unacceptable crossties to each other, a rating of the average integrity of the track as a percentage of desired integrity (the latter would be a characteristic of a track with all new crossties), and an evaluation of the life expectancy of and maintenance requirements for the track (including an appropriate retesting date).

The principal advantage of the crosstie-testing method of the present invention is, of course, that it avoids the need for a visual inspection of each tie while at the same time it greatly minimizes, if not eliminates altogether, the possibility of unnecessary crosstie replacements (and the concomitant economic losses) due to erroneous evaluations of the ties and the integrity of the track. This is clearly a beneficial result. Moreover, when the system is moving at a speed of about 2 miles per hour, which is relatively high compared to the speed at which an ordinary walking crosstie inspection can be performed, it is possible to achieve a testing rate in the neighborhood of as much as about 6,500 crossties per hour, in which case the implementation of the present invention not only entails the aforesaid advantages, i.e., no need for visual inspection and no likelihood of erroneous evaluation, but also enables the testing procedure to be carried out With greater assurance of correctness and at far higher speeds and rates than have heretofore been attainable.

BRIEF DESCRIPTION OF THE DRAWING

Further objects, features and advantages of the present invention will become apparent upon consideration of the following detailed description thereof when read in conjunction with the accompanying drawings, in which.

DETAILED DESCRIPTION OF THE INVENTION

Figure 1:
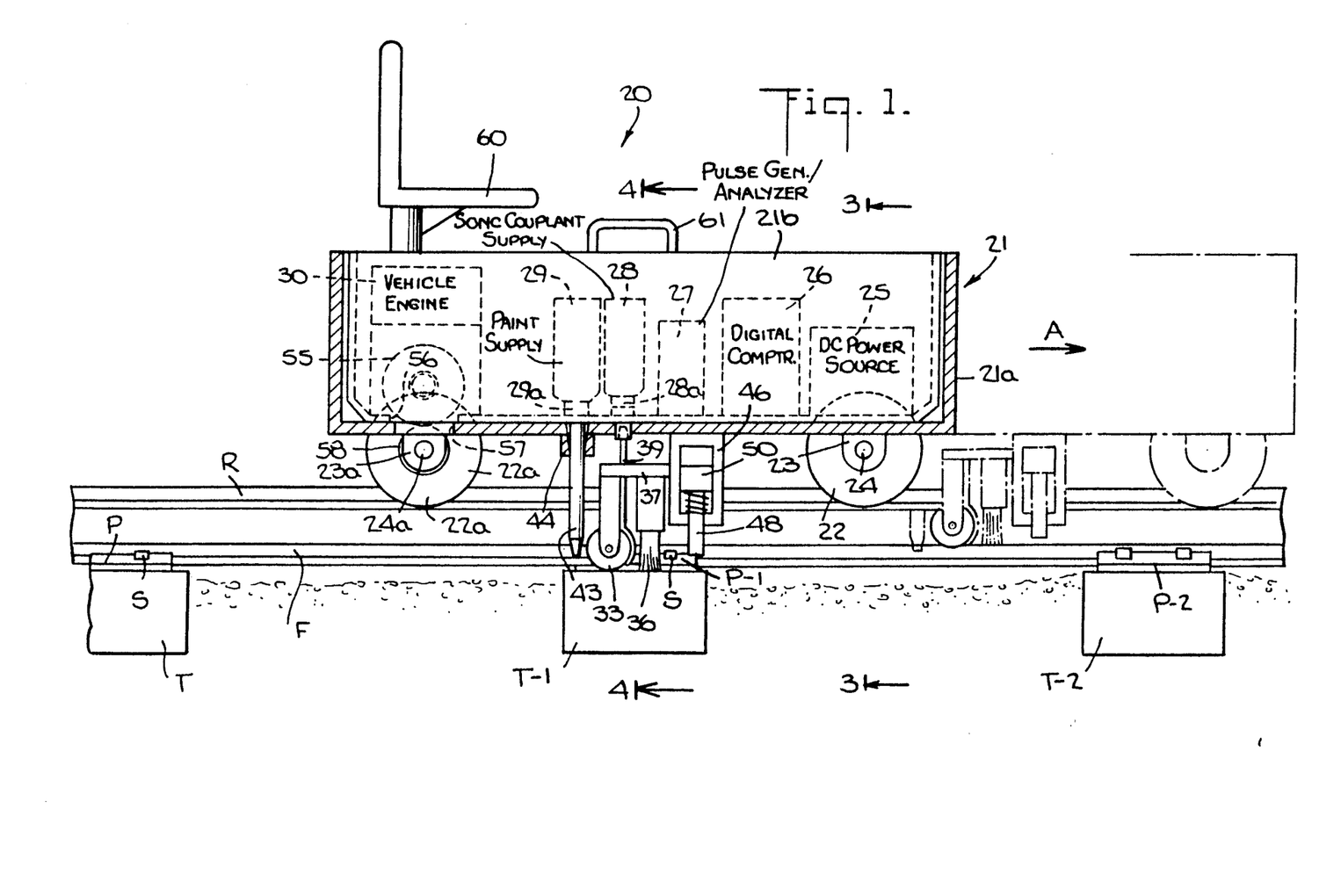
FIG. 1 is a schematic side elevational view, partly in section, of a vehicular crosstie-testing system according to one embodiment of the present invention.

Referring now to the drawing in greater detail, there is shown in FIG. 1 a vehicular device 20 according to the present invention for testing wood or concrete railroad crossties T, T-1, T-2, etc. The ties support the rails R on which the railroad cars ride, with the feet or base flanges F of the rails being received in suitable channels or recesses of respective tie plates P, P-1, P-2, etc. which are interposed between the rails and the top surfaces of the crossties and are secured to the underlying ties by suitable anchor bolts (not shown). The tie plates serve to locate the rails on the crossties and prevent them from spreading apart, with upward displacement of the rails relative to the crossties being inhibited by means of spikes S driven into the crossties through holes provided in the tie plates. In lieu of spikes, of course, suitable resilient clips (not shown) of the types described in U.S. Pat. Nos. 2,450,559, 3,004,716, 3,297,253 and 4,073,435 (and many others) may be used.

In the illustrated embodiment, the device 20 comprises a vehicle 21 constituted of a lightweight outer frame or body 21a, in the form of a rectangular open-topped container, and a lightweight inner frame or body 21b, likewise in the form of a rectangular open-topped container, seated in the outer body 21a. The vehicle 21 is adapted to ride on the rails R by means of paired sets of conventional flanged front and rear railway wheels 22, 22a, with the outer vehicle body 21a for this purpose being, merely by way of example, equipped at its bottom with front and rear journals 23, 23a providing bearings for the respective front and rear axles 24, 24a on which the wheels are mounted.

The device 20 further comprises, as schematically indicated in FIG. 1, a number of components which are located within the inner body 21b and a number which are located outside the outer body 21a. Among the former are a D.C. power source 25 (e.g., a battery), a digital computer 26 (e.g., a P.C.), an electrical pulse generator and analyzer 27, a sonic couplant liquid supply tank 28 which is equipped with a solenoid-controlled discharge valve 28a and with a pump (not shown), a paint or marking liquid supply tank 29 which is likewise equipped with a solenoid-controlled discharge valve 29a and with a pump (not shown), and an electric motor or engine 30 for driving the vehicle.

Figure 2:
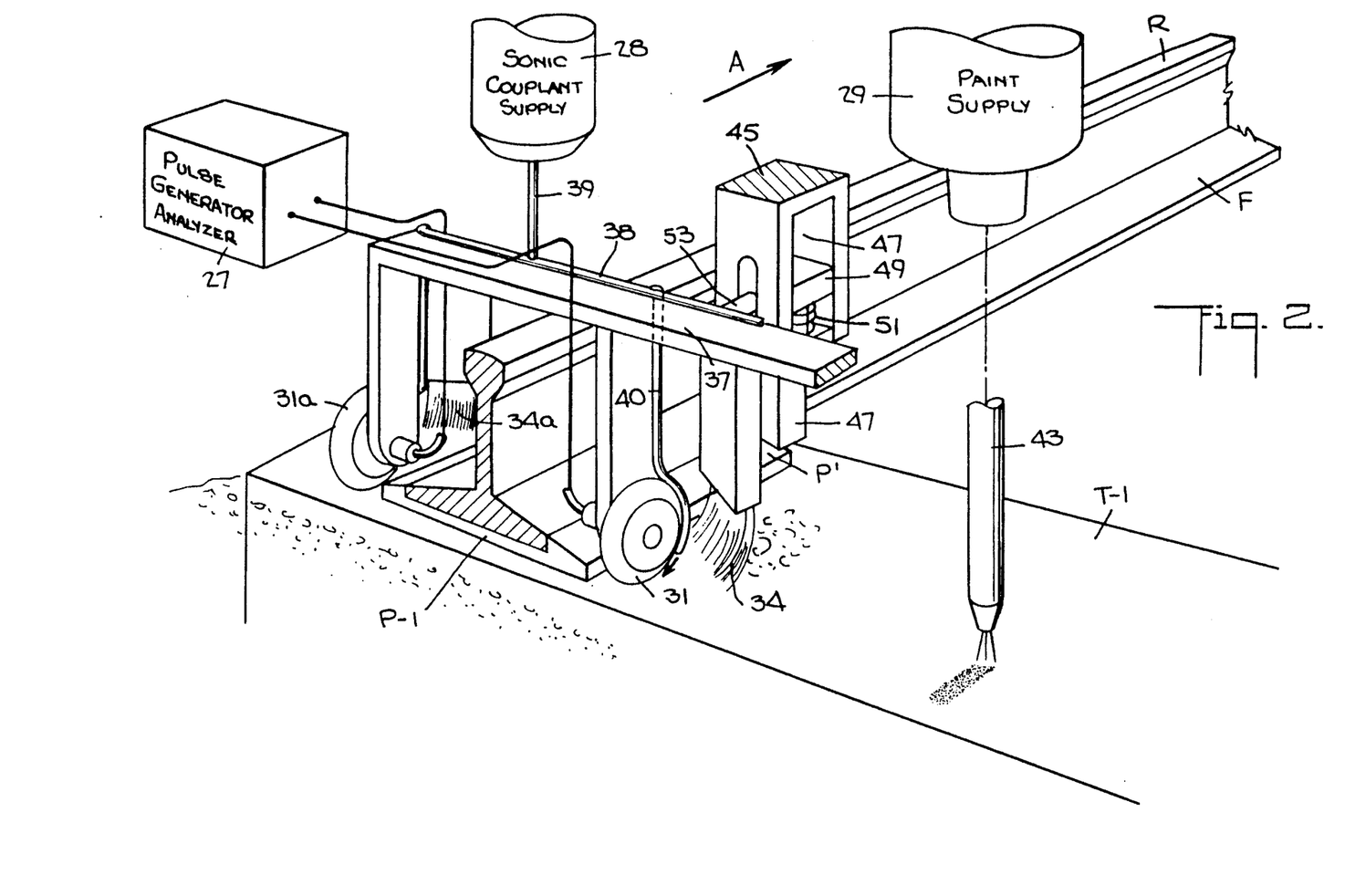
FIG. 2 is a fragmentary schematic illustration, in perspective, of certain of the operating elements of the crosstie-testing system shown in FIG. 1.
Figure 4:
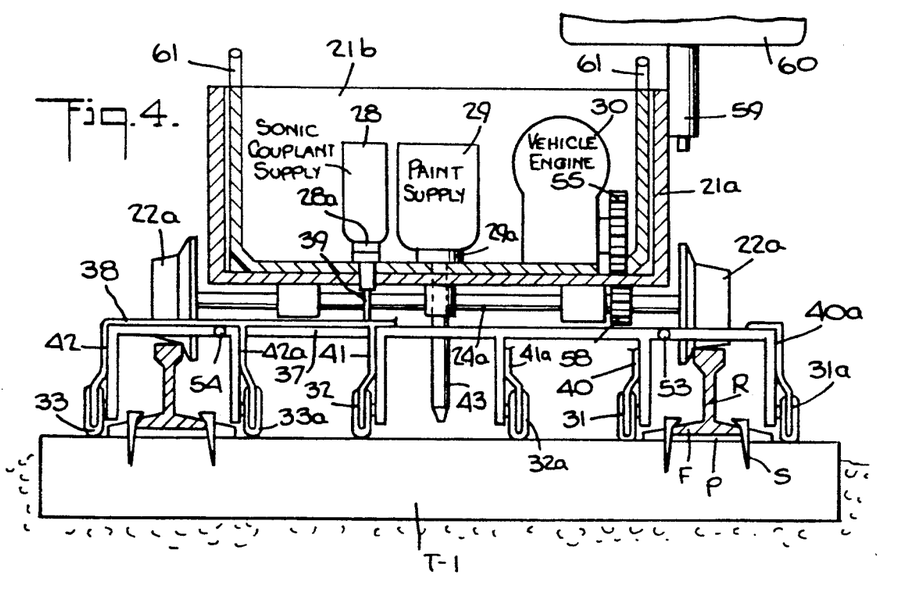
Figure 6:
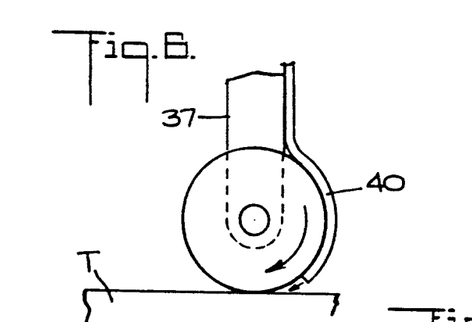
FIG. 6 is a fragmentary side elevational view, on an enlarged scale, of one of the rolling transducers shown in FIGS. 1-4 and shows a sonic couplant liquid feed tube for the same.
Figure 7:
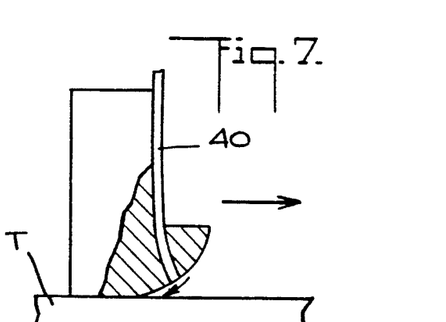
FIG. 7 is a similar fragmentary side elevational view of a somewhat modified standard transducer equipped for sliding contact with the crossties.

Among the components located outside the outer body 21b are three sets of paired rolling transducers 31/31a, 32/32a and 33/33a (see also FIGS. 2, 4 and 6), or alternatively three sets of sliding transducers of the type shown in FIG. 7, of which one transducer of each pair is designed for transforming electrical pulses received from the pulse generator into sonic mechanical pulses and for transmitting the mechanical pulses to a respective region of a crosstie being tested, while the other transducer of each pair is designed for sensing the mechanical pulses traveling through the tie region and transforming them back into electrical pulses for transmission to the pulse analyzer. There are also three sets of paired ballast sweeping brushes 34/34a, 35/35a and 36/36a, which are associated with and positioned in front of the respective pairs of transducers 31/31a, 32/32a and 33/33a as viewed in the direction of travel A of the vehicle 21. The two brushes of each pair are, as best shown in FIG. 2, oriented obliquely to the direction of movement of the vehicle, for example, at opposite angles of about 45° to the direction of movement, so as to sweep any ballast that may have accumulated on any given tie, either away from the rail or away from the mid-region of the tie, as the case may be, and thus to prevent any pile-up of ballast in those regions which could damage the oncoming transducers and interfere with the transmission of the sonic mechanical pulses to and from the ties.

The transducers and the ballast sweeping brushes are jointly supported by a vertically reciprocatable carrier frame 37 for enabling the transducers and the brushes to be jointly lowered and elevated so as to dispose their contact portions either at or away from the level of the top surfaces on the crossties. Although this retraction from the tie-top level is not absolutely essential, for example, when no ballast is present, as might be the case with train tracks running over bridges or trestles, the brushes and transducers could remain at the same level at all times, it does provide a potential benefit whenever ballast is present, in that it prevents the transducers from being damaged by unduly high accumulations of ballast in the spaces between ties where the brushes might not be fully effective and might fail to clear the ballast away.

In addition to the transducers and brushes, a manifold 38 is supported by the carrier frame 37 and establishes communication between an outlet duct 39 leading from the solenoid-controlled valve 28a of the couplant supply tank 28 and a set of three pairs of couplant feed tubes 40/40a, 41/41a and 42/42a. The feed tubes are arranged to enable the sonic couplant liquid to be pumped from the tank 28 onto the top surface of each crosstie directly along the paths of movement of the respective (see FIGS. 6 and 7). The couplant feed rate is generally less than 1 gallon per hour (but may be somewhat greater) and the thickness of the layer or film of couplant formed at the interface between each transducer and the tie surface is about 3 mils.

It should be noted, in passing, that the presence of the sonic couplant is deemed advisable because, at the most favorable frequencies of the sonic pulses, the same do not propagate through air. The sole purpose of the sonic couplant is to provide a liquid path to facilitate the travel of the sonic pulses from the transducers to the surface of the tie. Once inside the tie, of course, the pulses travel through the solid material (cellulosic cell walls and the lignin cell bonding material of a wood tie or grains of a concrete tie) without difficulty.

Also arranged exteriorly of the outer vehicle body 21a is a paint spray nozzle 43 which extends downwardly from the solenoid-controlled valve 29a of the paint supply tank 29. The nozzle is, however, not affixed to the outer vehicle body but rather is connected to the tank and extends slidably through a pair of aligned openings in the bottom walls of the inner and outer vehicle bodies and through a bushing 44 affixed to the outer body. The discharge end of the nozzle 43 is disposed at a level spaced somewhat from the level of the top surfaces of the ties.

Figure 3:
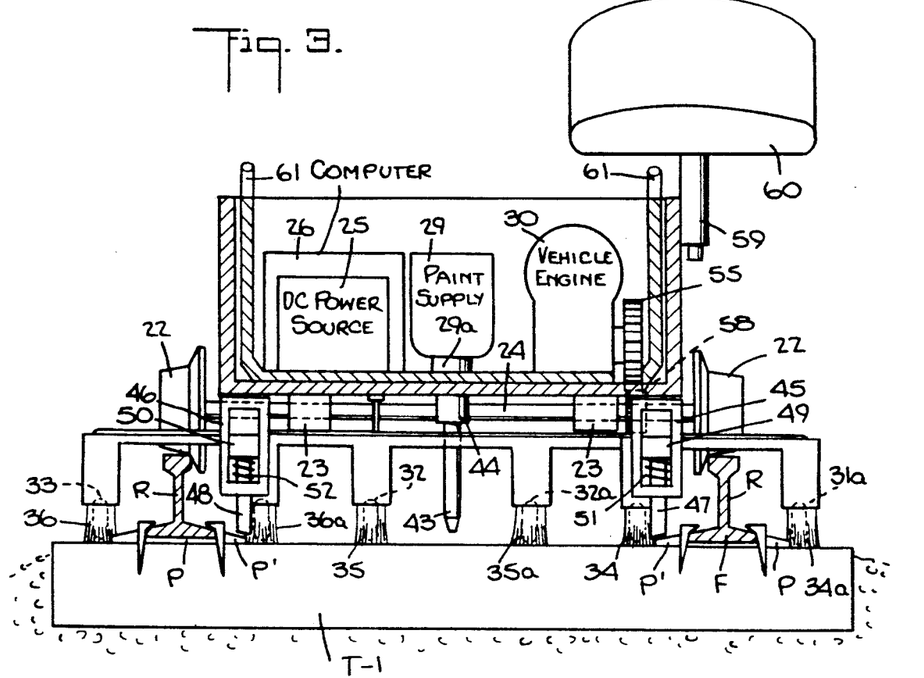
FIGS. 3 and 4 are, respectively, sectional views taken along the lines 3—3 and 4—4 in FIG. 1 and illustrate the system as utilizing three sets of paired transducers and associated ballast-sweeping brushes for contact with two test regions and one reference region of each crosstie, with the transducers and brushes being shown as lowered to the level of the top surfaces of the crossties.

To effect the up and down movements of the carrier frame 37 and of the transducers and brushes supported thereby, there are provided a pair of lift actuators 45 and 46 at the opposite side regions of the bottom wall of the outer vehicle body 21a. The actuators, which are located, as viewed in the direction of movement of the vehicle 21, just in advance of the ballast sweeping brushes 34 and 36a running along the insides of the two rails R (see FIGS. 2, 3 and 5), include respective tie plate sensors 47 and 48 in the form of relatively strong bar- or plate-shaped permanent magnets (they may, however, also be electromagnets). Each of the magnets is arranged approximately as far from the proximate edge of the associated rail flange F as the locus of the inside edges of the tie plates P, P-1, P-2, etc., and thus at its lowermost extremity each magnet will sense, i.e., be attracted to, only the inside side regions P, of the tie plates but not the rail flange. At their upper extremities, the magnets 47 and 48 are provided with or affixed to enlarged heads or blocks 49 and 50 which are slidably retained in the respective actuator housings, and respective springs 51 and 52 appropriately arranged in the actuator housings bear against the blocks and normally bias the same upwardly, thereby retaining the lower extremities of the magnets 47 and 48 spaced from the level of the upper surfaces of the tie plate regions P' by a distance somewhat greater than the extent of vertical travel of the carrier frame 37 required to bring the transducers and the ballast sweeping brushes into contact with the top surfaces of the crossties. The blocks 51 and 52 have respective rods or arms 53 and 54 (see FIGS. 2 and 4) extending laterally therefrom out of the actuator housings through respective guide slots, the arms being connected, exteriorly of the actuator housings, to the carrier frame 37.

Figure 5:
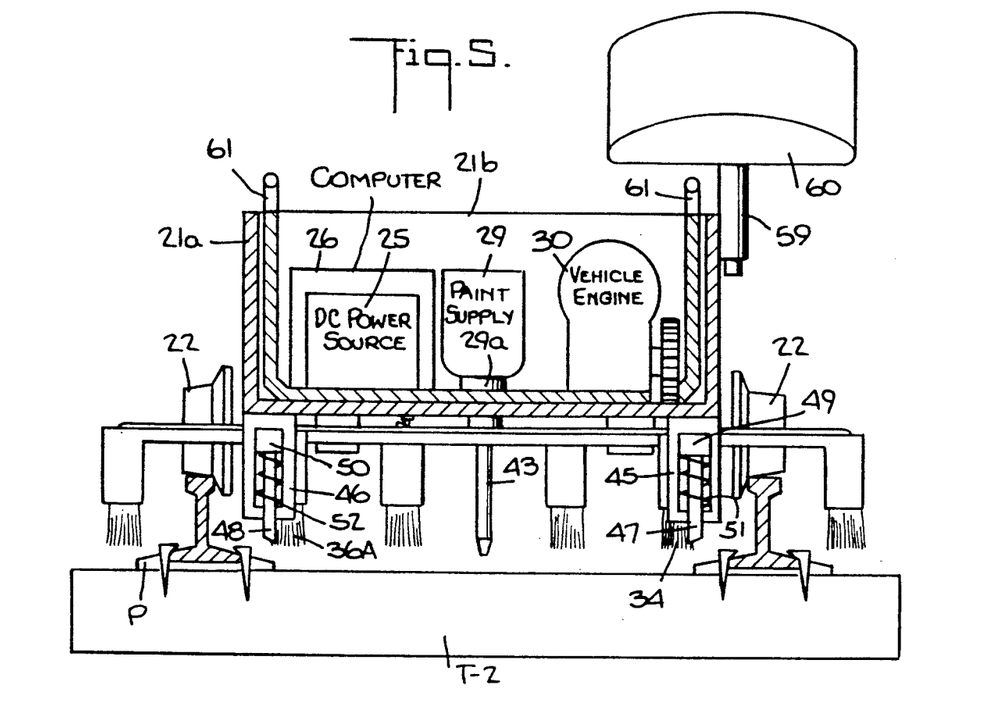
FIG. 5 is a sectional view similar to FIG. 3 but illustrates the same with the transducers and ballast-sweeping brushes retracted from the level of the top surfaces of the ties.

The operation of this arrangement is as follows. Initially, during a movement of the vehicle 21 in a crosstie-testing run along the track rails R, it may be assumed that the magnet sensors 47 and 48 are between two ties and approach the two tie plates on the second tie while in their retracted or elevated state (FIG. 5). Once the magnets are at least partly over those tie plates, they are attracted by and drawn downwardly toward the same against the force of the springs 51 and 52 and thereupon, optionally with a brief time delay, either correspondingly lower the carrier frame 37 along with the transducers and the ballast sweeping brushes or trigger a mechanism (not shown) for effecting that movement, the brushes by virtue of their locations ahead of the transducers engaging the tie first to clear it of ballast in the intended contact regions of the transducers (FIGS. 1-4). 4). Ultimately the magnets pass over the distal ends of the two tie plates and into the region overlying the gap between the just tested and the next to be tested crossties, whereupon the magnets are released after a brief time delay built into the system and the springs return the carrier frame to its elevated state, retracting the transducers and brushes from the level of the top surfaces and the crossties, the time delay built into the actuator system being sufficient to allow for retention of the transducers in contact with the tie across the full width thereof.

The vehicle 21 according to the embodiment of the invention illustrated in FIGS. 1-5 is, as previously indicated, self-propelled. To this end, the motor or engine 30 is provided with suitable gearing including an output or drive gear 55. The gear 55 is arranged so that, when the inner vehicle body 21b is disposed in the outer body 21a, the lowest part of the periphery of the gear projects through an opening 56 provided in the bottom wall of the inner body 21b of the vehicle and into an underlying aligned opening 57 provided in the bottom wall of the outer body 21a. In that position, the gear 55 meshes with a driven gear 58 keyed to or otherwise fixedly mounted on the rear axle 24a of the vehicle wheels 22a, enabling the motor to drive the vehicle along the track. The vehicle 21 is further provided at one side wall thereof with a bracket or bushing 59 which rotatably and/or removably supports an operator's seat 60. Although not expressly shown, it will be understood that the various operating controls required for activating the power source, the pulse generator, the computer, the motor, and the vehicle head- and tail-lights, if any, for regulating the motor speed (including braking), and for selecting specific functions (e.g., display, print-out, etc.) of the computer, will be provided in the vehicle at locations readily accessible to the tie inspector from the seat 60.

Figure 9:
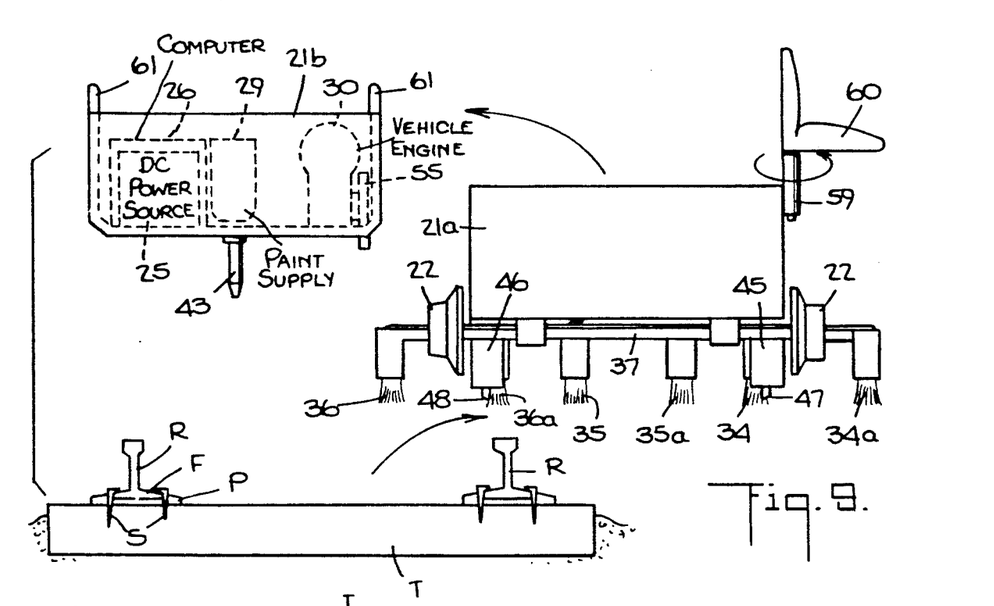
FIG. 9 is a schematic exploded view of the test vehicle of FIGS. 3 and 4, illustrating the vehicle and its operating components when separated for removal from the track.

As will be apparent to those skilled in the art, a crosstie-testing run as contemplated by the present invention may occasionally have to be interrupted or terminated relatively quickly either in order to permit a train to pass or in order to transport the vehicle to another test site. In either case, therefore, but especially when a train is approaching, the operator, as diagrammatically indicated in FIG. 9, must be able quickly to dismantle the test vehicle 21 and remove it from the track. To this end, the inner frame or body 21b may be lifted out of the outer body 21a, for example, with the aid of handles or grips 61 provided at the sides of the body 21b, after the seat 60 has been either removed or (as shown) rotated out of the way), and all cable connectors are of the quick-disconnect variety. Moreover, the inner and outer vehicle bodies, with the latter after extraction of the former having to be physically lifted off the rails, are both so constructed, in terms of size, weight and bulk, as to be easily handled by one person.

Figure 11:
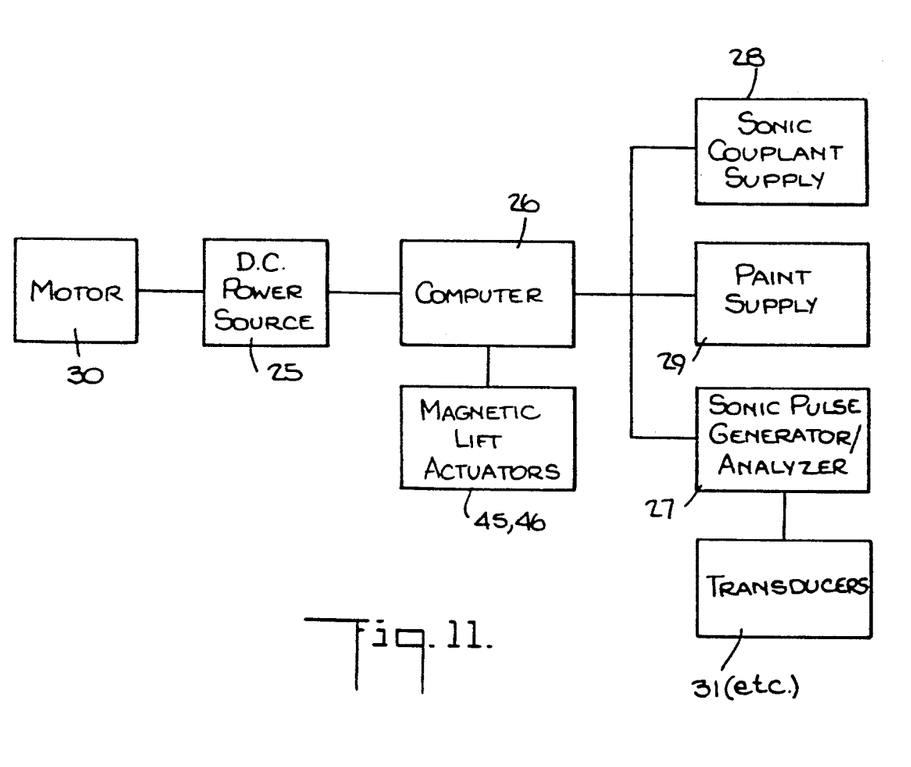
FIG. 11 is schematic block diagram illustrating the electrical interconnections between the various components of the system and the operational control exercised by the computer.

It will further be understood that the components of the system are operationally interconnected in any suitable manner, as indicated schematically in FIG. 11. Thus, the computer 26 both provides control signals to and receives data signals from the magnetic lift actuators 45 and 46, the sonic pulse generator and analyzer 27 (of which the generator part sends electrical pulses to the transmitting transducers 31 to 33 while the analyzer part receives and measures electrical pulses from the receiving transducers 31a to 33a corresponding to the sonic pulses sensed by the latter and transmits those measurements to the computer), the sonic couplant supply 28 and the marking paint supply 29. Specific circuitry for the various components and functions thereof has not been illustrated herein, as the features of the same are deemed to be well within the ken of any competent electrical engineer and circuit designer.

Figure 10:
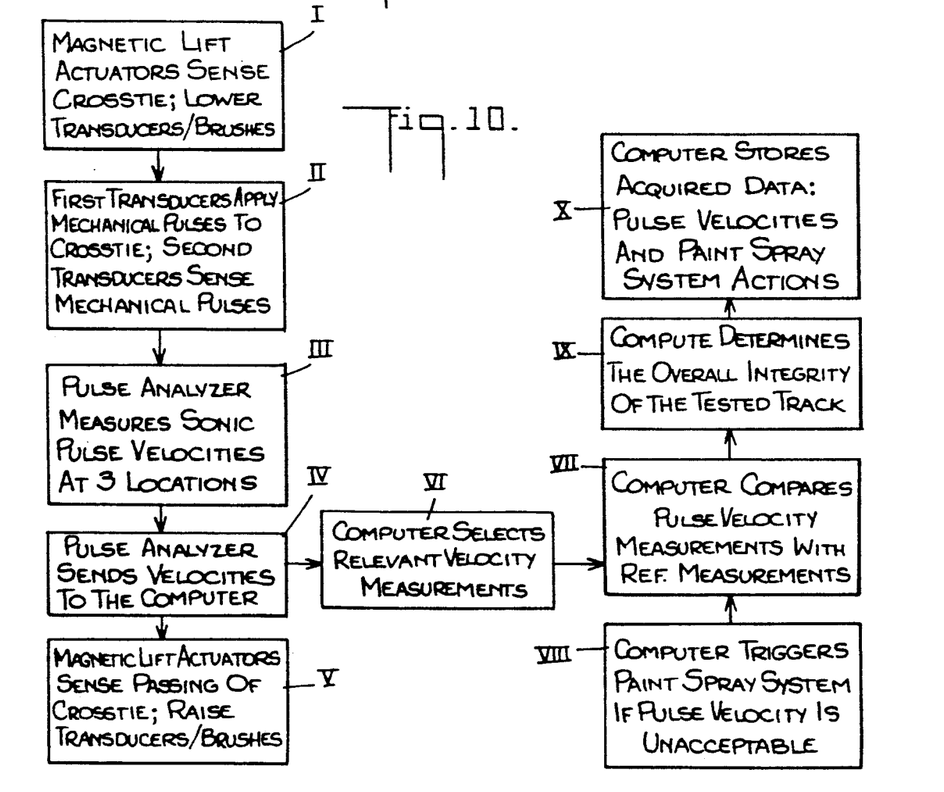
FIG. 10 is a flow chart illustrating the method of testing a/crosstie according to the present invention.

The operation of the crosstie-testing system according to the present invention is as follows, with reference being had also to the flow chart of the FIG. 10.

When sonic pulses travel through a material such as wood or concrete, their behavior is affected by the condition of the material; in particular, the velocity of the pulses and their ability to penetrate the material are reduced by changes in grain or cellular structure due, for example, to decay or other forms of deterioration and mechanical damage. These changes in behavior (loss of velocity and of ability to penetrate) can be measured electronically as long as the sonic pulses are of a frequency and initial velocity appropriate to the material being examined and are sent through the material along a specific path and at a suitable pulse repetition rate. The degree of loss of velocity and penetrating ability is proportional to the loss of integrity of the tested material.

As previously indicated, in accordance with the present invention the testing vehicle 21 moves along the track, the crossties of which are to be tested, preferably at a speed of approximately 2 mph although the speed can be somewhat higher (up to perhaps 15 or 20 mph) and is provided with six paired transducers, each pair being positioned to bracket or straddle a particular region of each crosstie. In particular, the two outside pairs of transducers are positioned to straddle the positions of the two tie-plates on each crosstie, and the middle pair of transducers are positioned to straddle a central region of the same crosstie. The two outside pairs of transducers thus straddle the regions of each tie most vulnerable to deterioration, while the middle pair of transducers straddles a region which is less vulnerable to deterioration, since the center region of the tie is less likely to be decayed and is not subject to load-induced mechanical destruction. It is for this reason that the center region of each tie is used as a reference for the physical condition of the tie. In this regard it will be understood, of course, that if a reference datum has been preprogrammed into the computer, the middle pair of transducers may be dispensed with, and that if readings of the crossties are to be taken along only one rail, then only one pair of transducers appropriately positioned on the vehicle 21 need be provided.

Reverting now to the operation of the illustrated vehicle 21 with six transducers, as the vehicle moves along the track, the lower extremities of the magnet sensors 47 and 48 come into the range of the proximal (i.e., the first encountered) edges of the inside regions P' of the tie plates on a given tie and are therefore attracted toward those tie plates. This correspondingly lowers the carrier frame 37 and the brushes and transducers supported thereby so as to dispose the contact regions of the brushes and transducers at the level of the top surface of the tie. At that point, stage I in FIG. 10 has been completed.

In stage II, as the vehicle 21 continues its movement, the brushes, Which are all located ahead of the transducers (the brushes 34 and 36a are, of course, not only located ahead of the associated transducers 31 and 33a but are also located behind the two lift actuators 45 and 46), come into contact with the respective surface regions of the tie and sweep any ballast or debris that may have accumulated on the tie in those regions ahead and sideways away from the paths of travel of the transducers. Thus, when the transducers come into contact with the top surface of the tie, the respective contact regions are clean and full contact between the transducers and the tie surface is ensured. As the transducers begin to move across tie surface, the computer 26, having received a signal indicating the lowering of the transducers, causes the valve 28a of the sonic couplant supply tank 28 to be opened and to permit the pump in the tank to deliver the sonic couplant liquid to the discharge duct 39 and thence via manifold 38 to the various couplant feed tubes 40 etc. for deposit onto the top surface of the crosstie along the paths of movement of the transducers.

As the transducers contact the top surface of the crosstie, the electrical pulses transmitted from the pulse generator to the transmitting transducers 31, 32 and 33 cause the same to generate corresponding mechanical pulses (to this end, the transducers incorporate respective piezoceramic disks or the like) and to transmit the same to the tie. The mechanical pulses then travel through the respective regions of the tie, from the transmitting transducers 31 and 33 to the associated receiving transducers 31a and 33a through the lateral tie-plate regions of the tie, which are designated by the legends "Test Scan 1" and "Test Scan 2" in FIG. 8, and from the transmitting transducer 32 to the receiving transducer 32a in the mid-region of the tie, which is designated by the legend "Reference Scan" in FIG. 8.

Figure 8:
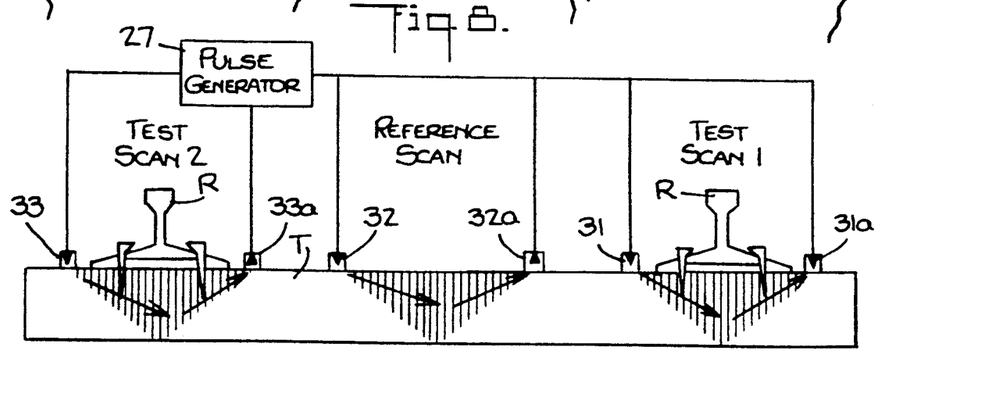
FIG. 8 is a diagrammatic representation of the pulse propagation through a crosstie during the performance of a tie-testing operation utilizing two test scans at the regions of the tie plates and a reference scan in the mid-region of the tie.

In each case, the sonic pulses or "waves" travel from the respective transmitting transducer to the associated receiving transducer, following the direction and pattern indicated by the shaded areas in FIG. 8. Thus, the respective series of sonic pulses cover the areas beneath the two tie plates and between the two "Reference Scan" transducers. The receiving transducers 31a, 32a and 33a thus sense the mechanical pulses traveling through the respective regions of the crosstie, and in the event of the existence of some degree of decay or deterioration in the regions beneath the tie plates, those pulses will be slower and more attenuated than the pulses travelling between the transducers 32 and 32a.

It should be pointed out here, that the selected speed of the vehicle 21 across the ties preferably is such as to enable the system to take a minimum of ten, and possibly as many as 25-50, velocity and attenuation measurements per crosstie. Thus, given that the average tie is 10 inches wide, that at a speed of 2 mph it takes the transducers 0.284 second to travel across the surface of a tie, and that it takes the pulses 100-500 microseconds to travel through the tie from the transmitting to the receiving transducer, a pulse repetition rate of 50 pulses per second is sufficient to enable the system to take 10 measurements per tie.

The receiving or sensing transducers 31a, 32a, and 33a transform the sensed mechanical pulses into electrical signals and transmit the same to the pulse analyzer part of the pulse generator/analyzer 27. In stage III, the pulse analyzer measures the sonic pulse velocities and degrees of attenuation at the three locations (as previously mentioned, the acoustic velocity in each case is obtained by dividing the known distance between each transmitting transducer and its associated receiving transducer by the time of travel of the sonic pulses from the transmitting to the receiving transducer, with the measurements being made by the electronic circuitry of the pulse analyzer) and then, in stage IV, sends the measurements to the computer 26. Thereafter, in stage V, the vehicle has travelled far enough to cause the magnetic sensors 47 and 48 to move past the distal (i.e., the second encountered) ends of the tie plates. This breaks the attraction between the magnets and the tie plates and permits the springs 51 and 52 to return the lift actuators back to the elevated position thereof shown in FIG. 5, which elevates the brushes and the transducers to a level above that of the top surfaces of the crossties while the vehicle moves across the gap between the previously tested crosstie and the next crosstie to be tested.

Concurrently therewith, in stage VI the computer selects the relevant velocity measurements; as previously described, in order to eliminate possible extreme deviations, the computer automatically discards unduly high and low velocity measurements and then, in stage VII, compares the average of the remaining readings taken at both tie plate locations with references reading taken at the center or midregion of the tie. If, at either tie plate location the reading is more than a predetermined tolerable percentage lower than the reference reading, the computer in stage VIII identifies the crosstie as unacceptable for continued service and triggers the paint spray system to cause a quantity of paint to be sprayed onto the crosstie for future identification. As also previously mentioned, the computer may be programmed to provide different types of signals to the paint spray system solenoid; for example, the computer may generate a long spray for totally unacceptable crossties, a somewhat shorter spray for crossties with a maximum life expectancy of, say, three years, and a still shorter spray for crossties with a maximum life expectancy of perhaps six years.

Concomitantly with the foregoing, the computer in stage IX makes a determination of the overall integrity of the tested track, which determination is updated at each crosstie passed by the vehicle. In this regard the computer identifies specific conditions relevant to track maintenance, including such as the proximity of unacceptable crossties to each other, the average integrity of the track expressed as a percentage of the desired integrity (which would be that of a track having all new crossties), the life expectancy of the track as a whole and consequent maintenance requirements, and an appropriate retesting date. Lastly, in stage X the computer stores the acquired data including the log of pulse velocities and paint spray systems actions and, upon demand, enables the data to be retrieved either on a screen or in a printed hard copy.

It will be understood that the foregoing description of preferred embodiments of the present invention is for purposes of illustration only, and that the various structural and operational features herein disclosed are susceptible to a number of modifications and changes none of which entails any departure from the spirit and scope of the present invention as defined in the hereto appended claims.

I claim:

1. A system for nondestructively testing and determining the condition and life expectancy of wood and concrete railroad crossties supporting on upper surfaces thereof the rails of a railroad track and the associated tie plates which are affixed to the crossties and are interposed between the upper surfaces of the crossties and the rails for locating the rails on the crossties, comprising:

a vehicle adapted to ride continuously at a speed of at least 2 miles per hour along a section of said track including a multiplicity of crossties to be tested;

means carried by said vehicle for generating first electrical pulses;

first and second transducer means carried by said vehicle and adapted to contact said upper surface of each of said crossties at first and second spaced locations a known distance apart and straddling a test region of each crosstie where damage and deterioration of the crosstie are likely to occur, said first transducer means being operable for receiving said first electrical pulses from said generating means and for transforming said first electrical pulses into sonic mechanical pulses and, when in contact with each crosstie, for transmitting said sonic mechanical pulses to said crosstie at said first location, and said second transducer means being operable for sensing said sonic mechanical pulses at said second location after said sonic mechanical pulses have passed through said test region and for transforming said sonic mechanical pulses into second electrical pulses;

means for receiving said second electrical pulses from said second transducer means and for analyzing said second electrical pulses and the sensed time of travel of said sonic mechanical pulses along said known distance between said first and second spaced locations, thereby to obtain measurements of the velocity and attenuation of said sonic mechanical pulses over the extent of said test region; and means responsive to said analyzing means for determining, from said measurements, the condition and life expectancy of each of said crossties and of the track as a whole.

2. A system as claimed in claim 1, wherein said determining means comprises a pre-programmed computer for comparing the pulse velocity and attenuation measurements with reference values therefor.

3. A system as claimed in claim 1, wherein said first and second transducer means are mounted on said vehicle for selective downward and upward movement into and out of contact with said upper surfaces of the crossties, and further comprising means for effecting such movements of said first and second transducer means.

4. A system as claimed in claim 3, wherein said means for effecting said downward and upward movements of said first and second transducer means comprise magnetic sensing means responsive to proximity or remoteness, respectively, of a tie plate on a crosstie.

5. A system as claimed in claim 3, further comprising first and second brush means mounted on said vehicle and located, respectively, in advance of said first and second transducer means as viewed in the direction of movement of said vehicle along, the track for clearing accumulated ballast and debris off said upper surface of each crosstie to be contacted by said first and second transducer means.

6. A system as claimed in claim 5, wherein said first and second brush means are mounted on said vehicle for selective downward and upward movement into and out of contact with said upper surfaces of the crossties, and further comprising means for effecting such movements of said first and second brush means.

7. A system as claimed in claim 6, wherein said means for effecting said downward, and upward movements of said first and second brush means comprise magnetic sensing means responsive to proximity or remoteness, respectively, of a tie plate on a crosstie.

8. A system as claimed in claim 1, further comprising means carried by said vehicle and controlled by said determining means for depositing onto any crosstie, the condition of which has been determined to be such as to render that crosstie unacceptable for further service, a quantity of paint signaling a need for replacement of that crosstie.

9. A system as claimed in claim 1, further comprising means carried by said vehicle and controlled by said determining means for depositing onto any crosstie the condition of which has been determined to be such as to render that crosstie fit only for less than unrestricted service, a quantity of paint signaling by the amount thereof the life expectancy of that crosstie.

10. A system as claimed in claim 1, further comprising means carried by said vehicle and controlled by said determining means for depositing onto said upper surface of each crosstie and under said first and second transducer means a pair of thin films of a liquid sonic couplant for a enhancing the transmission of said sonic mechanical pulses to and from that crosstie.

11. A system as claimed in claim 1, wherein said first and second transducer means comprise three pairs of transducers, with each such pair including one transmitting transducer and one receiving transducer, said transmitting and receiving transducers of one of said pairs being positioned on said vehicle to contact each crosstie at first and second spaced locations adjacent the opposite sides of one of the tie plates on that crosstie, said transmitting and receiving transducers of a second of said pairs being positioned on said vehicle to contact each crosstie at first and second spaced locations adjacent the opposite sides of the other of the tie plates on that crosstie, the portions of each crosstie under said tie plates each constituting a respective test region, and said transmitting and receiving transducers of the third pair being positioned on said vehicle to contact each crosstie at first and second spaced locations adjacent the opposite sides of the mid-region of that crosstie, said mid-region of each crosstie constituting a reference region thereof.

12. A system as claimed in claim 11, wherein all of said transmitting and receiving transducers are mounted on said vehicle for joint selective downward and upward movement into and out of contact with said upper surfaces of the crossties, and further comprising means for effecting such movements of said transmitting and receiving transducers.

13. A system as claimed in claim 12, wherein said means for effecting said downward and upward movements of said transmitting and receiving transducers comprise magnetic sensing means responsive to proximity or remoteness of the tie plates on each crosstie.

14. A system as claimed in claim 11, further comprising a plurality of brushes carried by said vehicle and each located in advance of a respective one of said transmitting and receiving transducers as viewed in the direction of movement of said vehicle along the track for clearing accumulated ballast and debris off each crosstie to be contacted by said transmitting and receiving transducers.

15. A system as claimed in claim 14, wherein said brushes are mounted on said vehicle for joint selective downward and upward movement into and out of contact with said upper surfaces of the crossties, and further comprising means for effecting such movements of said brushes.

16. A system as claimed in claim 15, wherein said means for effecting said downward and upward movements of said brushes comprise magnetic sensing means responsive to proximity or remoteness of the tie plates on the crossties.

17. A method for nondestructively testing and determining the condition and life expectancy of wood and concrete railroad crossties supporting on upper surfaces thereof the rails of a railroad track and the associated tie plates which are affixed to the crossties and are interposed between the crossties and the rails for locating the rails on the crossties, comprising the steps of:

moving a vehicle, which is equipped with a pulse generator, at least one pair of first and second transducers, a pulse analyzer, and a computer continuously at a speed of at least about 2 miles per hour along a section of a track including a multiplicity of crossties to be tested;

generating first electrical pulses, and applying said first electrical pulses to said first transducer;

bringing said first and second transducers into contact with said upper surface of each of said crossties at, respectively, first and second spaced locations a known distance apart and straddling a test region of each cross-tie where damage and deterioration of the crosstie are likely to occur;

activating said first transducer for transforming said first electrical pulses into sonic mechanical pulses and for transmitting the latter to each of said crossties at the respective first location thereon;

activating said second transducer for sensing said sonic mechanical pulses at the respective second location on each crosstie after they have passed through the respective test regions and for transforming said sensed sonic mechanical pulses into second electrical pulses;

analyzing said second electrical pulses received from said second transducer and the sensed time of travel of said sonic mechanical pulses along said known distance between said first and second spaced locations on each crosstie, thereby to obtain measurements of the velocity and attenuation of said sonic mechanical pulses over the extent of said test regions, and feeding the results to said computer; and determining by means of said computer, from said measurements, the condition and life expectancy of each of said crossties and of the track as a whole.

* * * * *